(12) United States Patent
Miller

(10) Patent No.: US 8,100,949 B2
(45) Date of Patent: Jan. 24, 2012

(54) TRANSVERSE ROD CONNECTORS WITH OSTEOCONDUCTIVE MATERIAL

(75) Inventor: Keith E. Miller, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 805 days.

(21) Appl. No.: 12/132,278

(22) Filed: Jun. 3, 2008

(65) Prior Publication Data

US 2009/0299413 A1 Dec. 3, 2009

(51) Int. Cl.
*A61B 17/70* (2006.01)

(52) U.S. Cl. ......................................... 606/278

(58) Field of Classification Search .............. 606/278
See application file for complete search history.

(56) References Cited

U.S. PATENT DOCUMENTS

| | | | |
|---|---|---|---|
| 4,781,183 A | 11/1988 | Casey et al. | |
| 5,108,399 A | 4/1992 | Eitenmuller et al. | |
| 5,522,816 A * | 6/1996 | Dinello et al. | 606/252 |
| 6,187,005 B1 | 2/2001 | Brace et al. | |
| 6,554,832 B2 | 4/2003 | Shluzas | |
| 6,592,585 B2 | 7/2003 | Choi et al. | |
| 6,616,668 B2 * | 9/2003 | Altarac et al. | 606/252 |
| 6,736,817 B2 * | 5/2004 | Troxell et al. | 606/252 |
| 6,752,807 B2 * | 6/2004 | Lin et al. | 606/250 |
| 6,761,721 B2 * | 7/2004 | Burgess et al. | 606/252 |
| 6,887,241 B1 * | 5/2005 | McBride et al. | 606/86 A |
| 7,029,474 B2 | 4/2006 | Richelsoph et al. | |
| 7,077,844 B2 | 7/2006 | Michelson | |
| 7,104,993 B2 | 9/2006 | Baynham et al. | |
| 7,175,622 B2 | 2/2007 | Farris | |
| 7,291,152 B2 | 11/2007 | Abdou | |
| 2005/0059972 A1 | 3/2005 | Biscup | |
| 2006/0079895 A1 | 4/2006 | McLeer | |
| 2006/0276788 A1 | 12/2006 | Berry et al. | |
| 2007/0185492 A1 | 8/2007 | Chervitz et al. | |
| 2007/0213720 A1 | 9/2007 | Gordon et al. | |
| 2007/0225713 A1 | 9/2007 | Altarac et al. | |
| 2007/0270805 A1 | 11/2007 | Miller et al. | |
| 2007/0270809 A1 | 11/2007 | Drewry et al. | |
| 2007/0270972 A1 | 11/2007 | Gordon et al. | |
| 2007/0276380 A1 | 11/2007 | Jahng et al. | |
| 2009/0248076 A1 * | 10/2009 | Reynolds et al. | 606/246 |

* cited by examiner

*Primary Examiner* — Pedro Philogene

(57) ABSTRACT

The present application is directed to transverse connectors that connect first and second vertebral rods that extend along the spine. In one embodiment, the transverse connector includes an elongated base with a first receiver at a first section of the base to receive the first vertebral rod, and a second receiver at a second section of the base to receive the second vertebral rod. Osteoconductive material is positioned on at least the first receiver.

13 Claims, 4 Drawing Sheets

TRANSVERSE ROD CONNECTORS WITH OSTEOCONDUCTIVE MATERIAL

BACKGROUND

The present application is directed to transverse rod connectors and, more particularly, to rod connectors that include osteoconductive material.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve.

Vertebral rods may be implanted to support and position vertebral members in one or more of these regions. The rods extend along a section of the spine and are connected to the vertebral members with one or more fasteners. The rods may have a curved configuration to conform to the curvature of the spine. Often times two or more rods are connected together and work in combination to support and position the vertebral members. The rods may have the same or different shapes and sizes depending upon their position along the spine. The vertebral rods may be used during fusion of two or more vertebral members.

One or more transverse connectors may attach the rods together for further stabilization and positioning. The connectors have a first connection to the first rod, and a second connection to the second rod.

One drawback is that transverse connectors can sometimes increase the possibility of a failed fusion between two or more of the vertebral members. It is commonly believed that the transverse connectors disrupt the bony fusion mass that forms during fusion and therefore creates a weak point in the fusion.

SUMMARY

The present application is directed to transverse connectors that connect first and second vertebral rods that extend along the spine. In one embodiment, the transverse connector includes an elongated base with a first receiver at a first section of the base to receive the first vertebral rod, and a second receiver at a second section of the base to receive the second vertebral rod. Osteoconductive material is positioned on at least the first receiver.

The various aspects of the various embodiments may be used alone or in any combination, as is desired.

DETAILED DESCRIPTION

Figure 1:
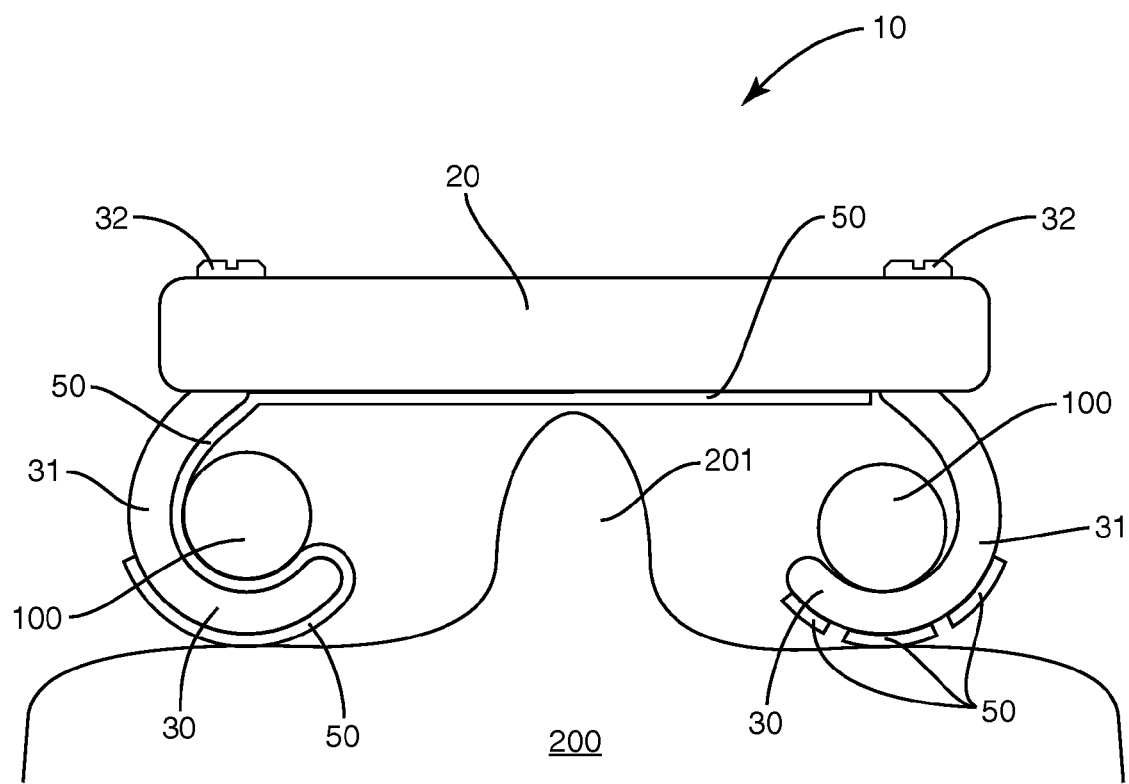
FIG. 1 is a schematic side view of a transverse connector connected to vertebral rods according to one embodiment.

The present application is directed to transverse connectors with osteoconductive material to facilitate fusion between vertebral members. FIG. 1 illustrates a schematic view of a transverse connector 10 that includes a base 20 and receivers 30. The base 20 is sized to extend across a section of the spine. In the embodiment of FIG. 1, the base 20 includes a length to span across a spinous process 201 of the vertebral member 200. Receivers 30 are positioned on each end of the base 20. Receivers 30 are adapted to engage with one of the vertebral rods 100. One or both of the base 20 and receivers 30 include osteoconductive material 50 to facilitate bone growth along the spine in the area of the transverse connector 10.

Figure 2:
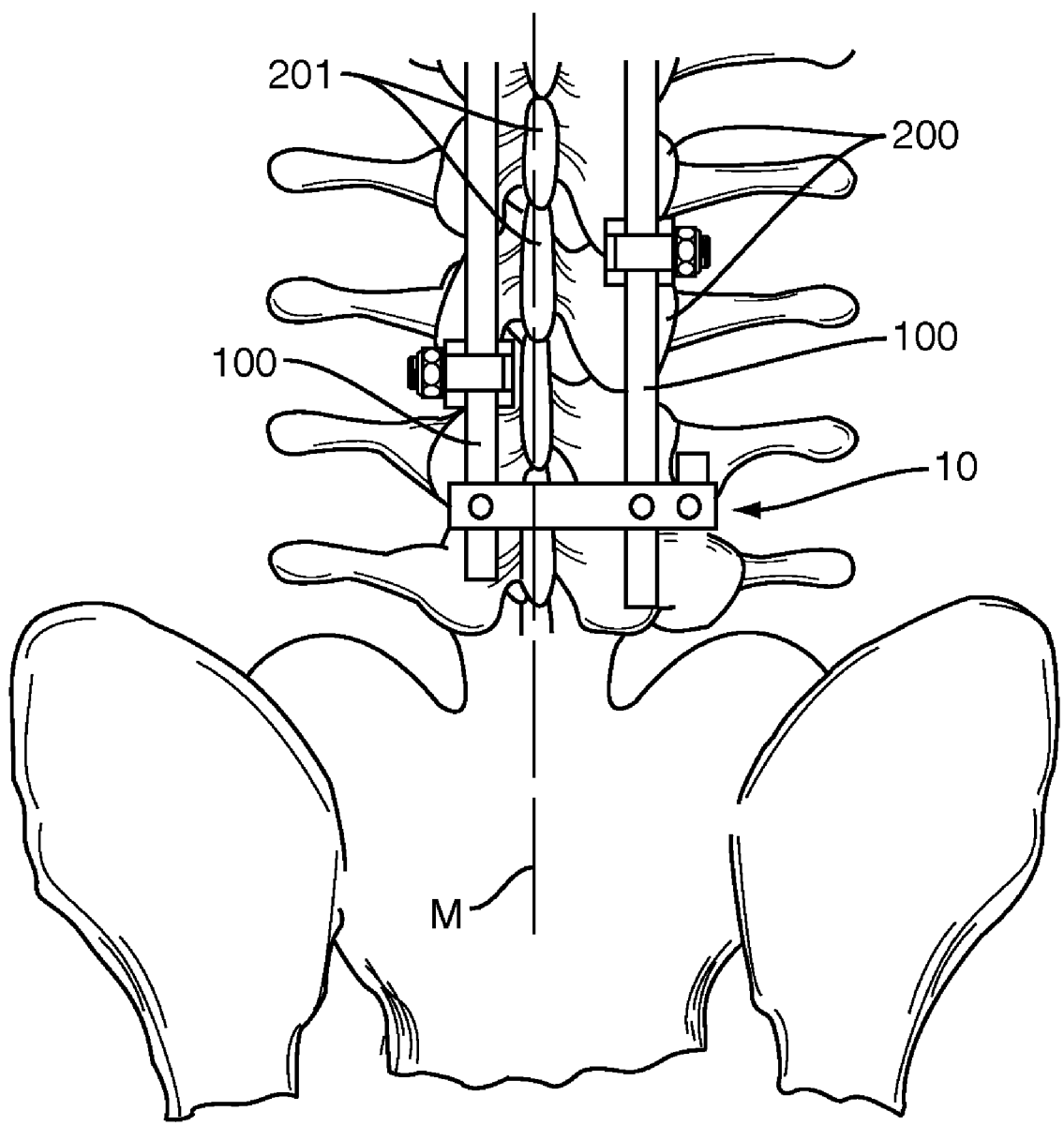
FIG. 2 is a front view of a transverse connector connected to a pair of vertebral rods according to one embodiment.

FIG. 2 illustrates an embodiment with a pair of vertebral rods 100 extending along a length of the spine. The transverse connector 10 extends between and attaches to each of the rods 100. In this embodiment, the rods 100 extend along the spine on opposite sides of the midline M that extends through the spinous processes 201 of the vertebral members 100. The transverse connector 10 may also be used in contexts with more than two vertebral rods 100, and to connect rods 100 positioned on one side of the midline M.

Figure 3:
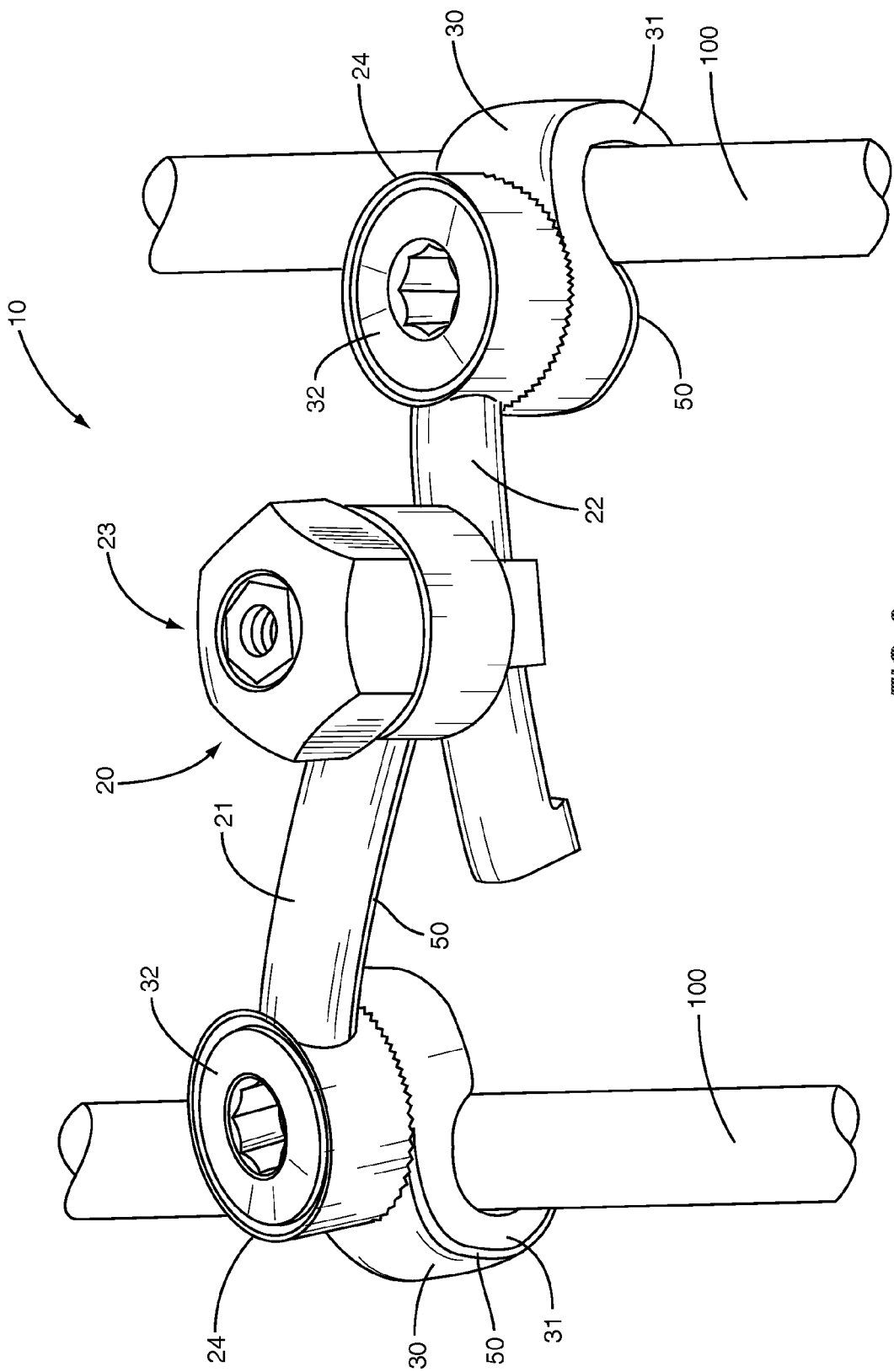
FIG. 3 is a perspective view of a transverse connector connected to a pair of vertebral rods according to one embodiment.
Figure 4:
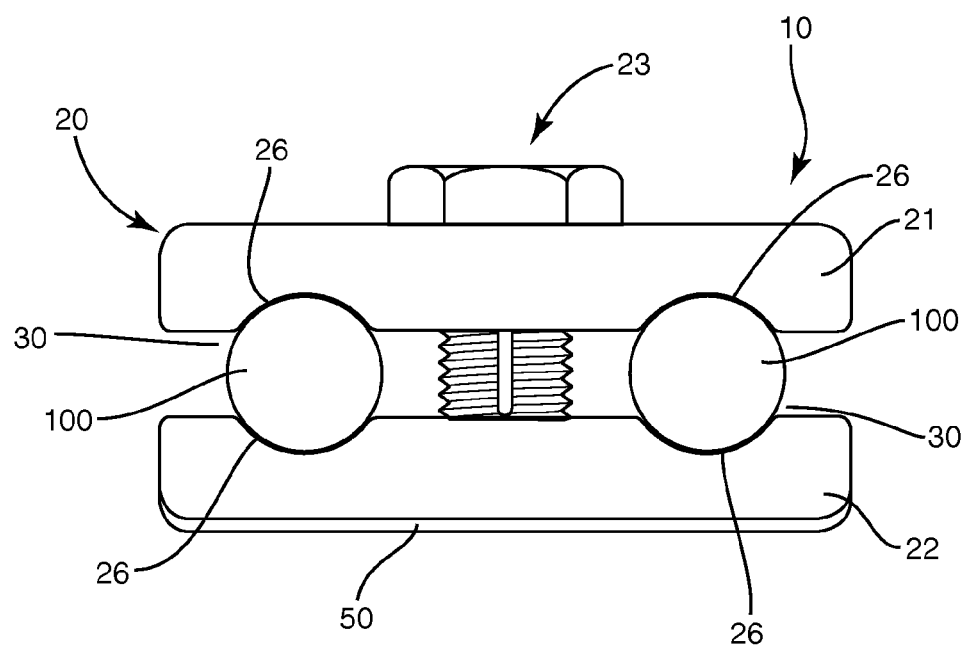
FIG. 4 is a side view of a transverse connector connected to a pair of vertebral rods according to one embodiment.

The base 20 may include a variety of shapes and sizes. Base 20 may be curved or may be substantially straight. In one embodiment as illustrated in FIGS. 1 and 2, base 20 is a single, unitary member. FIG. 3 illustrates another embodiment with the base 20 formed from separate members including a first member 21 and a second member 22. The members 21, 22 are connected together by a fastener 23. Fastener 23 also provides for positioning the members 21, 22 at various angles to accommodate the vertebral rods 100. FIG. 4 illustrates another embodiment with the base 20 formed by first and second members 21, 22 that are positioned in an overlapping arrangement with the first member 21 positioned above the second member 22 (i.e., the first member 21 is posterior to the second member 22 when the connector 10 is positioned within the patient). Each member 21, 22 includes scallops 26 that align together to form the receivers 30 that receive the vertebral rods 100.

Figure 5:
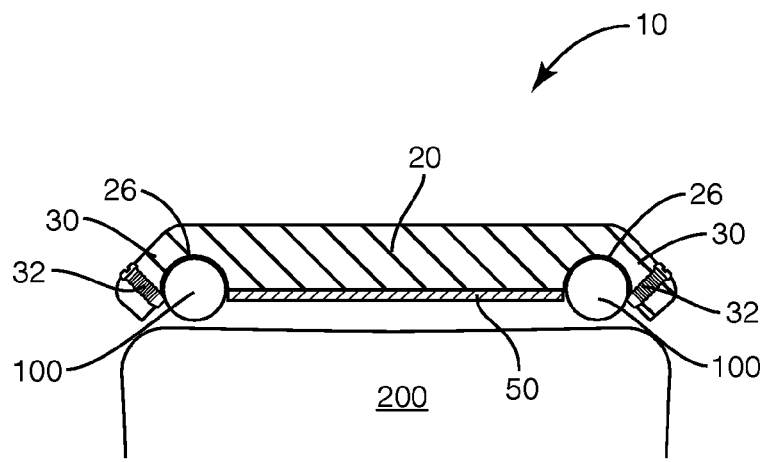
FIG. 5 is a sectional view of a transverse connector connected to a pair of vertebral rods according to one embodiment.

The receivers 30 are adapted to engage with the vertebral rods 100. The receivers 30 may include arms 31 as illustrated in FIGS. 1 and 3. Each of the arms 31 is shaped to extend around at least a portion of the vertebral rod 100. The arms 31 may be attached to the base 20 by fasteners 32. Receivers 30 may also be formed by the base 20. FIG. 4 illustrates one embodiment with the receivers 30 formed between members 21, 22 of the base 20. FIG. 5 illustrates another embodiment with the ends of the base 20 being shaped to form receivers 30. In these various embodiments, each of the receivers 30 positioned along the base 20 may be the same or different.

The receivers 30 may be located relative to the vertebral members 200 and the vertebral rods 100 in different manners. FIGS. 1 and 4 include embodiments with the receivers 30 shaped to fit between the vertebral rods 100 and the vertebral members 200. FIG. 5 includes an embodiment with the receivers 30 positioned away from the vertebral member 200.

Examples of connectors 10 are disclosed in U.S. Patent Application Publications 2007/0270818 and 2007/0173829, each incorporated herein by reference.

The osteoconductive material 50 is positioned to facilitate bone growth that results in a stronger fusion mass. The osteoconductive material 50 provides a substrate for attachment of bone and is positioned in areas that will cause a stronger fusion mass. In one embodiment, the osteoconductive material 50 is coated across the entire connector 10 that includes the base 20 and receivers 30. In other embodiments, the osteoconductive material 50 is on just isolated elements or sections of the elements.

FIG. 1 includes an embodiment with the under sides of the receivers 31 and sections of the base 20 are coated with osteoconductive material 50. The coating may be applied in a similar manner to each lateral side of the connector 10, or may be applied in different manners. By way of example, the osteoconductive material 50 is continuously coated across the left receiver arm 31 of FIG. 1, and discretely coated onto sections of the right receiver arm 31 of FIG. 1. The osteoconductive material 50 is also coated across the entire under side of the base 20. FIG. 4 includes the osteoconductive material 50 applied across the entire under side of member 22 that contacts against the vertebral member 200. FIG. 5 includes the osteoconductive material 50 applied to the under side of the base 20.

In the various embodiments, the connector 10 may include a single type of osteoconductive material 50, or may include two or more different types of osteoconductive material 50.

Figure 6:
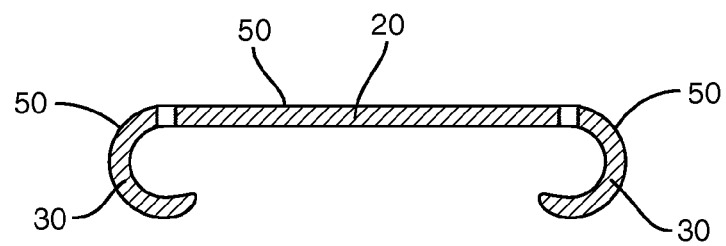
FIG. 6 is a sectional view of a transverse connector constructed from an osteoconductive material according to one embodiment.

In one embodiment as illustrated in FIG. 6, the base 20 and the receivers 30 are constructed from an osteoconductive material 50. In one embodiment, the entire base 20 and receivers 30 are constructed from the same osteoconductive material 50. In another embodiment, sections of the base 20 and/or receivers 30 are constructed from the osteoconductive material 50. In another embodiment, the base 20 and/or receivers 30 are constructed from two or more different osteoconductive materials 50.

In some embodiments, particular sections of the connector 10 do not include osteoconductive material 50 because they may interfere with the structural workings. In the embodiment of FIG. 1, the threaded sections of the base 20 that receive the fasteners 32 are not coated because it may interfere with the threads. In the embodiment of FIG. 3, member 22 may not be coated to allow for the member 22 to be movable for adjusting a distance between the receivers 30.

A variety of osteoconductive materials 50 may be applied to the connector 10. One type of material is a fill material that may be used to attach the connector 10 to the vertebral rods 100. Examples of fill materials include demineralized bone matrix (DBM), bi-calcium phosphate matrix, platelet gel, calcium phosphate-based materials, methomathactuloid, cranial plast, ceramics, polymers, calcium-sulfate, hydroxyapatite, tricalcium phosphate, or one or more of the previous in combination.

Another type of material is osteoinductive and/or osteogenic material that forms bone and may improves the connection with the cortical bone tissue at the outer shell of the vertebral members 100. Examples of osteogenic materials 40 include hydroxyapatite, bone morphogenetic protein (BMP), LIM mineralized proteins (LMP), DBM, platelet gel, osteoinductive peptides, growth factors, pharmaceutical agents such as antibiotics, pain medication, anti-inflammatory drugs, steroids, or one or more of the previous in combination. The osteoconductive material 50 may also include a combination of the fill and osteogenic materials.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. In one embodiment, the osteoconductive material 50 is positioned away from the fastener 32 to faciliate subsequent removal of the fastener 32. The present embodiments are, therefore, to be considered in all respects as illustrative and not restrictive, and all changes coming within the meaning and equivalency range of the appended claims are intended to be embraced therein.

What is claimed is:

1. A transverse connector to connect first and second vertebral rods comprising:
    a base with an elongated length to extend between the vertebral rods;
    a first receiver at a first end of the base to receive the first vertebral rod;
    a second receiver at a second end of the base to receive the second vertebral rod;
    osteoconductive material positioned on just bottom sides of the first and second receivers with a remainder of the first and second receivers being devoid of the osteoconductive material.

2. The connector of claim 1, wherein the first and second receivers include identical shapes.

3. The connector of claim 1, wherein the osteoconductive material is positioned along just a bottom side of a first section of the base at the first end and just a bottom side of a second section of the base at the second end.

4. The connector of claim 1, wherein the osteoconductive material is positioned along just a bottom side of the base to be located between the base and at least one vertebral member with a remainder of the base being devoid of the osteoconductive material.

5. The connector of claim 1, wherein the osteoconductive material is hydroxyapatite.

6. The connector of claim 1, further comprising a second osteoconductive material positioned on at least one of the first and second receivers.

7. A transverse connector to connect first and second vertebral rods comprising:
    an elongated base with a first member having a first section and a separate second member having a second section;
    a first receiver at the first section of the base to receive the first vertebral rod;
    a second receiver at the second section of the base to receive the second vertebral rod, the second section being spaced apart from the first section;
    osteoconductive material positioned on just the first member; and
    a fastener that movably connects the first section and the second section, the osteoconductive material being spaced away from the fastener.

8. A transverse connector to connect first and second vertebral rods comprising:
    an elongated member with a length to extend between the first and second vertebral rods, the member including a first section that connects to the first vertebral rod and a second section that connects to the second vertebral rod, the first and second sections being spaced apart along the elongated member; and osteoconductive material positioned on just the first section.

9. The connector of claim 8, wherein each of the first and second sections include a curved shape that conforms respectively to one of the first and second vertebral rods.

10. The connector of claim 8, wherein the osteoconductive material includes a first area and a second area each positioned on the first section and being spaced apart.

11. The connector of claim 8, wherein the osteoconductive material is positioned just on a bottom surface of the first section.

12. A transverse connector to connect first and second vertebral rods comprising:

an elongated member with a first end adapted to connect to the first vertebral rod and a second end adapted to connect to the second vertebral rod, the ends being shaped to extend around at least a portion of the vertebral rods and be placed between the rods and a vertebral member; and osteoconductive material positioned on just the first and second ends of the elongated member, the osteoconductive material being limited to being positioned between the vertebral rods and the vertebral member.

13. The connector of claim 12, further comprising a second osteoconductive material positioned on one of the first and second ends.

* * * * *